(12) United States Patent
Shirata et al.

(10) Patent No.: US 9,995,726 B2
(45) Date of Patent: Jun. 12, 2018

(54) LUBRICANT DETERIORATION SENSOR AND OPTICAL SENSOR

(71) Applicant: NABTESCO CORPORATION, Tokyo (JP)

(72) Inventors: Takuya Shirata, Tokyo (JP); Yasuhito Ida, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 0 days. days.

(21) Appl. No.: 15/030,783

(22) PCT Filed: Oct. 27, 2014

(86) PCT No.: PCT/JP2014/078485
§ 371 (c)(1),
(2) Date: Apr. 20, 2016

(87) PCT Pub. No.: WO2015/060457
PCT Pub. Date: Apr. 30, 2015

(65) Prior Publication Data
US 2016/0252490 A1 Sep. 1, 2016

(30) Foreign Application Priority Data

Oct. 25, 2013 (JP) ................. 2013-222381

(51) Int. Cl.
*G01N 33/28* (2006.01)
*G01N 21/25* (2006.01)
*G01N 21/59* (2006.01)
*G01N 21/85* (2006.01)

(52) U.S. Cl.
CPC ......... *G01N 33/2888* (2013.01); *G01N 21/25* (2013.01); *G01N 21/255* (2013.01); *G01N 21/5907* (2013.01); *G01N 21/8507* (2013.01)

(58) Field of Classification Search
CPC ........ G01N 21/27; G01N 21/21; G01N 21/50; G01N 21/25; G01N 33/28; G08B 17/10
See application file for complete search history.

(56) References Cited

U.S. PATENT DOCUMENTS

| | | | |
|---|---|---|---|
| 3,076,375 A | 2/1963 | Donnell | |
| 2008/0246623 A1* | 10/2008 | Nagashima | G01N 21/21 340/630 |
| 2012/0086942 A1* | 4/2012 | Honda | G01N 21/27 356/436 |

FOREIGN PATENT DOCUMENTS

| | | |
|---|---|---|
| EP | 0 026 093 A1 | 4/1981 |
| GB | 1427795 A | 3/1976 |

(Continued)

OTHER PUBLICATIONS

International Preliminary Report on Patentability and the Written Opinion of the International Searching Authority as issued in International Patent Application No. PCT/JP2014/078485, dated Apr. 26, 2016.

(Continued)

*Primary Examiner* — Jamil Ahmed
(74) *Attorney, Agent, or Firm* — Pillsbury Winthrop Shaw Pittman, LLP

(57) ABSTRACT

One object is to provide a lubricant deterioration sensor that can maintain accuracy of sensing the deterioration of a lubricant having low transmissivity and an optical sensor used therein for sensing the amount of received light. The lubricant deterioration sensor is used for determining deterioration state of a lubricant. The lubricant deterioration sensor includes an optical sensor having: an LED for emitting detection light; an oil entering gap in which the detection light passes through a lubricant to be inspected; a color sensor for sensing color information of the detection light having passed through the lubricant; and a logarithmic (Continued)

amplifier for logarithmically amplifying the detection value sensed by the color sensor and outputting the amplified detection value.

10 Claims, 10 Drawing Sheets

(56) References Cited

FOREIGN PATENT DOCUMENTS

| | | |
|---|---|---|
| JP | S62-238444 A | 10/1987 |
| JP | H02-210247 A | 8/1990 |
| JP | H08-114547 A | 5/1996 |
| JP | 2000-292345 A | 10/2000 |
| JP | 2012-117951 A | 6/2012 |
| JP | 2013-195206 A | 9/2013 |
| WO | WO 2010/150526 A1 | 12/2010 |

OTHER PUBLICATIONS

International Search Report as issued in International Patent Application No. PCT/JP2014/078485, dated Jan. 20, 2015.
Supplementary European Search Report EP Application No. 14 85 5875.2 dated May 29, 2017.
C.V. Ossia et al., "Novel Chromatic Technique Based on Optical Absorbance in Characterizing Mineral Hydraulic Oil Degradation", Advances in Tribology, 2012, pp. 1-8.

* cited by examiner

LUBRICANT DETERIORATION SENSOR AND OPTICAL SENSOR

CROSS-REFERENCE TO RELATED APPLICATIONS

This application is the U.S. National Stage of PCT/JP2014/078485, filed Oct. 27, 2014, which in turn claims priority to Japanese Patent Application No. JP2013-222381, filed Oct. 25, 2013. The contents of these applications are incorporated herein by reference in their entireties.

TECHNICAL FIELD

The present invention relates to a lubricant deterioration sensor used to detect the deterioration state of a lubricant and an optical sensor used therein for sensing the amount of received light.

BACKGROUND

Lubricant deterioration sensors have conventionally detected the light absorbance of the three primary colors in a visible light passing through a lubricant to determine the deterioration level of the lubricant based on the light absorbance of the three primary colors (see Japanese Patent Application Publication No. 2012-117951).

The lubricant deterioration sensor disclosed in Japanese Patent Application Publication No. 2012-117951 includes a void portion receiving a lubricant, an LED for emitting visible light into the void portion, and a color sensor for receiving light from the LED having passed through the void portion. In the lubricant deterioration sensor, the LED emits light and the color sensor receives the light and outputs a sensing result on a device provided outside.

RELEVANT REFERENCES

Patent Literature

Patent Literature 1: Japanese Patent Application Publication No. 2012-117951

SUMMARY

The above lubricant deterioration sensor includes a linear amplifier as an operational amplifier for amplifying a voltage value outputted from the color sensor. In FIG. 10, transmissivity is taken on the abscissa consisting of a logarithmic axis, and the color sensor output (detection value) is taken on the ordinate. Supposing that a new lubricant results in a transmissivity value of one and a color sensor output value of one, lower transmissivity leads to sharply decreased color sensor output, as shown in FIG. 10. Both the transmissivity and the color sensor output in FIG. 10 are in arbitrary units. In a region where the transmissivity is low, the amount of change of the color sensor output is extremely small with respect to an amount of change of the transmissivity, and thus there is possibility that the transmissivity cannot be accurately determined from the color sensor output value. Therefore, for a lubricant prone to stain and used in a region of low transmissivity, the deterioration state is sensed at lower accuracy as compared to lubricants used in a region of high transmissivity. Accordingly, there is a demand for a lubricant deterioration sensor that can maintain accuracy of sensing the deterioration state of a lubricant having low transmissivity.

The present invention is made in view of such circumstances, and one object thereof is to provide a lubricant deterioration sensor that can maintain accuracy of sensing the deterioration state of a lubricant having low transmissivity, that is, under the condition of a small amount of light sensed. Another object of the present invention is to provide an optical sensor capable of sensing the difference in amount of light.

Means and its effects for achieving the object will be now described. To overcome the above problem, a lubricant deterioration sensor used for sensing a deterioration state of a lubricant comprises: an inspection unit for receiving a lubricant to be inspected; a light emitting element for emitting detection light into the inspection unit; a light receiving element for obtaining a detection value indicating color information of the detection light having passed through the lubricant; and a logarithmic amplifier for amplifying the detection value with a logarithmic function and outputting the amplified detection value.

In the above arrangement, the detection light emitted from the light emitting element may pass through the lubricant in the inspection unit, and the light receiving element may sense the color information of the detection light having passed through the lubricant. The detection value sensed by the light receiving element may be amplified by a logarithmic amplifier with a logarithmic function and outputted. The detection value amplified by the logarithmic amplifier may change largely relative to the amount of change of the transmissivity in the region of low transmissivity as compared to the detection value amplified by the linear amplifier. Therefore, the transmissivity can be accurately determined from the detection value. Accordingly, it may be possible to maintain accuracy of sensing the deterioration state of a lubricant having low transmissivity.

The lubricant deterioration sensor may preferably further include a collimator lens for producing parallel light rays disposed between the light emitting element and the inspection unit. In the above arrangement, the collimator lens for producing parallel light rays may be disposed between the light emitting element and the inspection unit. The detection light emitted from the light emitting element may be transformed by the collimator lens into parallel light rays, which can reach the light receiving element with restricted diffusion and convergence. Thus, the amount of light received by the light receiving element may be large enough to stabilize the sensing accuracy.

The lubricant deterioration sensor may preferably further include a determination unit configured to calculate brightness from the detection value and determine that the lubricant has been deteriorated if the absolute value of the amount of change of the brightness per unit time is larger than a predetermined value.

Since the lubricant deterioration sensor may provide a detection value amplified by the logarithmic amplifier, the amount of change of the detection value can be grasped in the region of low transmissivity. In the above arrangement, it may be determined that the lubricant has been deteriorated if the absolute value of the amount of change of the brightness or the maximum color-component difference per unit time is larger than a predetermined value. Therefore, the determination can be accurately made from the amount of change of the brightness or the maximum color-component difference per unit time. It may be possible to grasp rapid deterioration of a lubricant and abnormality in a machine.

The lubricant deterioration sensor may preferably further include a determination unit configured to calculate a maximum color-component difference and determine that the lubricant has been deteriorated if the amount of change of the maximum color-component difference per unit time is a negative value.

Since the lubricant deterioration sensor may provide a detection value amplified by the logarithmic amplifier, the amount of change of the detection value can be grasped in the region of low transmissivity. In the above arrangement, it may be determined that the lubricant has been deteriorated if the amount of change of the maximum color-component difference per unit time is a negative value. Therefore, the determination can be accurately made from the amount of change of the maximum color-component difference per unit time. It may be possible to grasp rapid deterioration of a lubricant and abnormality in a machine.

The lubricant deterioration sensor may preferably further include a determination unit configured to calculate brightness and a maximum color-component difference from the detection value and determine that the lubricant has been deteriorated if the amount of change of the maximum color-component difference per unit brightness is a negative value.

In the above arrangement, it may be determined that the lubricant has been deteriorated if the amount of change of the maximum color-component difference per unit brightness is a negative value. Therefore, the determination can be made more accurately than the case where the deterioration of the lubricant is determined from at least one of the brightness and the maximum color-component difference.

The determination unit of the lubricant deterioration sensor may preferably determine that the lubricant has been deteriorated if the absolute value of the amount of change of the brightness is larger than a predetermined value and the brightness is smaller than the oil deterioration threshold value for determining deterioration of the lubricant.

In the above arrangement, it may be determined that the lubricant has been deteriorated if the absolute value of the amount of change of the brightness is larger than a predetermined value and the brightness is smaller than the oil deterioration threshold value. Therefore, the deterioration of the lubricant can be determined accurately from the amount of change of the brightness and the brightness itself.

The determination unit of the lubricant deterioration sensor may preferably determine that a machine is damaged if the absolute value of the amount of change of the brightness is larger than a predetermined value and the brightness is smaller than a machine damage threshold value for determining damage to the machine on which the lubricant deterioration sensor is installed In the above arrangement, it may be determined that the lubricant has been deteriorated if the absolute value of the amount of change of the brightness is larger than a predetermined value and the brightness is smaller than a machine damage threshold value. Therefore, the damage to the machine can be determined accurately from the amount of change of the brightness and the brightness itself.

An optical sensor capable of overcoming the above problem may sense the amount of light having passed through an inspection object and amplify the amount of light by a logarithmic amplifier, wherein an output voltage from the logarithmic amplifier is in a logarithmic relationship with an input voltage to the logarithmic amplifier.

In the above arrangement, even with low transmissivity of an inspection object such as a cooling oil or a lubricant, that is, even with a small amount of light sensed, it may be possible to sense the difference in amount of passing light produced from the difference in transmissivity.

It may be preferable that the optical sensor senses the amounts of two or more primary colors of light among the three primary colors of light and a logarithmic amplifier is provided for each of the two or more primary colors.

In the above arrangement, even if the sensors for sensing the amounts of the primary colors of light have different properties, the logarithmic amplifiers provided for individual primary colors may be designed to cancel the difference between the properties. Particularly in determining the deterioration state of a lubricant using the output from the optical sensor, there is no need of using different determination algorithms for each primary color.

In the above optical sensor, the logarithmic amplifier may preferably be disposed rearward of the light receiving surface of the light receiving element for sensing the amount of light, with respect to the direction of the light incident on the light receiving surface. Additionally, the logarithmic amplifier may be provided directly on the light receiving element, or an intermediate such as a circuit substrate of the optical sensor may be placed between the logarithmic amplifier and the light receiving surface of the light receiving element.

In the above arrangement, the length of a wire between the light receiving element and the logarithmic amplifier may be minimized to make the whole size compact and minimize the external noise effect.

ADVANTAGES

The present invention enables sensing the difference in amount of light and maintaining accuracy of sensing the deterioration state of a lubricant having low transmissivity, that is, under the condition of a small amount of light sensed.

DESCRIPTION OF EXAMPLE EMBODIMENTS (First Embodiment)

A first embodiment of a lubricant deterioration sensor and an optical sensor installed therein will be hereinafter described with reference to FIGS. 1 to 5. The lubricant deterioration sensor may be installed on a machine using a lubricant, which is an inspection object, and configured to determine the deterioration of the lubricant and the damage to the machine. When a movable component that requires a lubricant is damaged, impurity substances may penetrate in the lubricant by friction or the like. Thus, damage to the machine can be determined from the state of the lubricant. In this embodiment, the lubricant may include a hydraulic oil.

Figure 1:
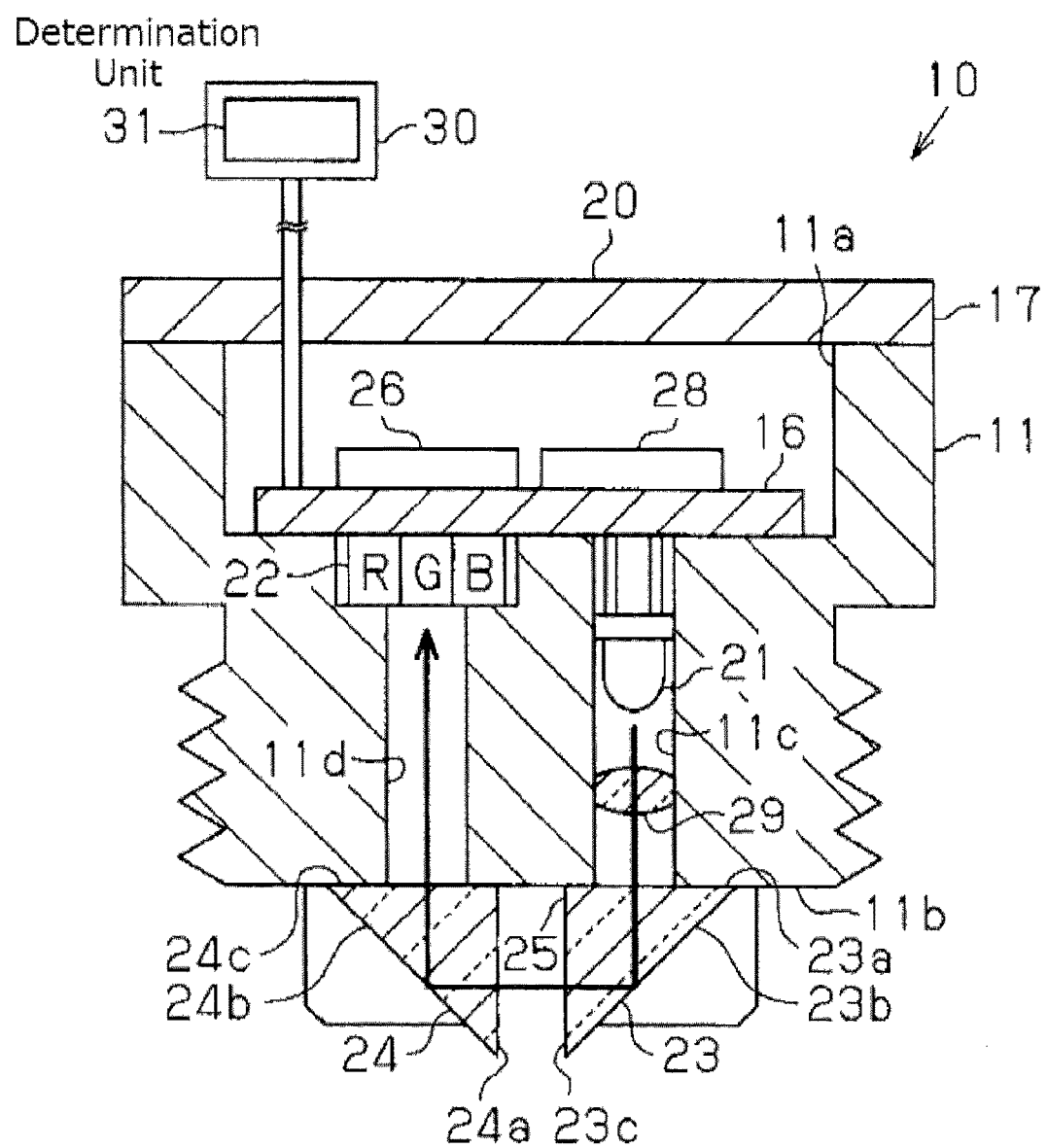
FIG. 1 is a sectional view showing a schematic structure of a first embodiment of a lubricant deterioration sensor.

The structure of the lubricant deterioration sensor 10 will now be described with reference to FIG. 1, along with the structure of the optical sensor 20. Referring to FIG. 1, the lubricant deterioration sensor 10 may include an optical sensor 20 and a personal computer (PC) 30. That is, the PC 30 may not be included in the structure of the optical sensor 20. The optical sensor 20 may include a column-shaped housing 11 made of metal or resin. A container section 11a may be provided in an upper area of the housing 11. The container section 11a may be covered with a cover 17. An external thread 11a may be formed in the outer circumference of a lower area of the housing 11. The lubricant deterioration sensor 10 may be mounted on the machine with the external thread.

The container section 11a may contain a circuit substrate 16. The circuit substrate 16 may be fixed on the housing 11. On the bottom surface of the circuit substrate 16, there may be an LED (light emitting diode) 21 as a light emitting element and a color sensor 22 as a light receiving element arranged adjacent to each other. On the top surface of the circuit substrate 16, there may be arranged a logarithm amplifier 26 and an LED driver 28. Additionally, various kinds of electronic components may be installed on the circuit substrate 16 but are not shown. The logarithmic amplifier 26 may be positioned (on a back surface) to face the color sensor 22 across the circuit substrate 16. Thus, the length of a wire between the color sensor 22 and the logarithmic amplifier 26 may be minimized to make the whole size compact and minimize the external noise effect.

The LED 21 may be a known device for emitting white light to be sensed. The color sensor 22 may be an RGB sensor that may output R value (corresponding to red), G value (corresponding to green), and B value (corresponding to blue) as color information in accordance with the amounts of light of wavelengths for red, green, and blue colors in the sensed light. The logarithmic amplifier 26, in which an output voltage and an input voltage may be in a logarithmic relationship, may be provided for each color. The R value, G value, and B value outputted from the color sensor 22 may be inputted into the logarithmic amplifier as input voltages and amplified with a logarithmic function such that the output voltages may be in a logarithmic relationship with the input voltages, and outputted to the determination unit 31 disposed outside. The LED driver 28 may adjust the electric current to the LED 21 for driving.

The color sensor 22 in this embodiment may sense the amounts of red, green, and blue light; or alternatively, the color sensor 22 may sense the amounts of any one or two colors of light. The LED 21 and the color sensor 22 may be individually selected in accordance with the color to be sensed.

The red, green, and blue colors may be independently sensed; or alternatively, the sum of the amounts of the three colors or any two of the three colors of light may be sensed. The outputs from the logarithmic amplifiers corresponding to the colors may be summed up by an operational amplifier; or alternatively, the values corresponding to the colors outputted from the color sensor 22 may be summed up by an operational amplifier and inputted to the logarithmic amplifier 26.

The determination unit 31 may determine whether the lubricant has been deteriorated and whether the machine has been damaged, based on the detection value. The personal computer (PC) 30 may be connected to the lubricant deterioration sensor 10 to serve as the determination unit 31.

The housing 11 may have a first through hole 11c extending in an optical axis direction of the detection light. The first through hole 11c may extend from the bottom of the container section 11a to the bottom of the housing 11. A first prism 23 may be provided on the bottom of the housing 11 at an exit of the first through hole 11c. The first prism 23 may be a right-angle prism made of a translucent material such as quartz and glass. The first prism 23 may have an incident surface 23a where the detection light having traveled through the first through hole 11c enters, a reflection surface 23b where the detection light having entered from the incident surface 23a is reflected, and an exit surface 23c through which the detection light reflected at the reflection surface 23b exits out.

The incident surface 23a and the exit surface 23c may be optical-polished. The reflection surface 23b may be formed of a metal deposited film and a protection film. The metal deposited film is, for example, a thin aluminum film and formed on the outer side of the translucent material. The protection film is, for example, a silicon dioxide thin film or a magnesium fluoride thin film formed on the outer side of the metal deposited film to protect the metal deposited film. An angle of the reflection surface 23b with respect to the incident surface 23a may be set such that a light path of the light entering the reflection surface 23b is reflected at 90 degrees from the incident direction.

A collimator lens 29 for producing parallel light rays may be provided between the LED 21 and the first prism 23 of the first through hole 11c. The collimator lens 29 may transform the detection light emitted from the LED 21 into parallel light rays with restricted diffusion and convergence.

A second prism 24 may be provided on the bottom 11b of the housing 11. The second prism 24 may be disposed with a gap from the first prism 23. The second prism 24 may have the same structure as the first prism 23 and have an incident surface 24a, a reflection surface 24b, and an exit surface 24c. The gap between the first prism 23 and the second prism 24 may be an oil entering gap 25 where the lubricant enters and stays therein and the gap may serve as an inspection unit.

The housing 11 may have a second through hole 11d extending in parallel with the first through hole 11c. The second through hole 11d may extend from the bottom of the container section 11a to the bottom 11b of the housing 11 and may be disposed between the second prism 24 and the color sensor 22.

The white detection light emitted from the LED 21 may travel straight through the first through hole 11c and enters the first prism 23. The light path of the detection light is then bent at 90 degrees by the reflection surface 23b and enters the oil entering gap 25 from the exit surface 23c. The detection light further penetrates the lubricant in the oil entering gap 25 and then enters the second prism 24. The light path of the detection light having entered the second prism 24 may be bent at 90 degrees by the reflection surface 24b and then the detection light may travel straight through the second through hole 11d. Finally, the detection light may be received by the color sensor 22. In other words, the light path of the detection light emitted from the LED 21 may be reversed at 180 degrees by the first prism 23 and the second prism 24. The detection light that has traveled through the lubricant may have a wavelength region thereof corresponding to the hue of the oil absorbed.

Figure 2:
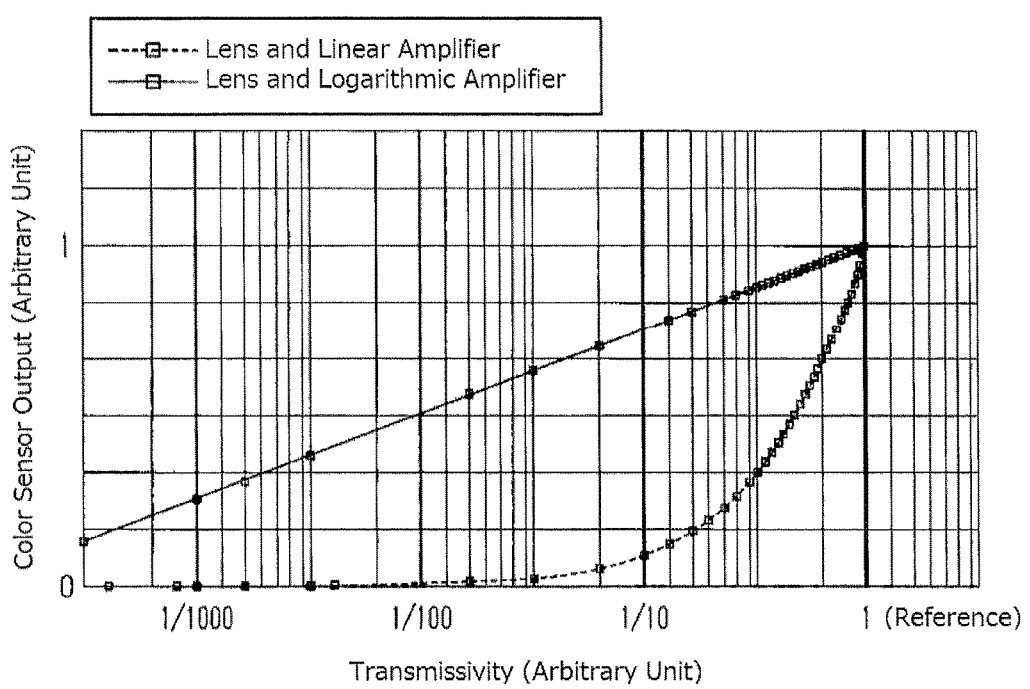
FIG. 2 shows the relationship between transmissivity and the output of a color sensor in the same embodiment of the lubricant deterioration sensor.

FIG. 2 shows a color sensor output from a linear amplifier and a color sensor output from the logarithmic amplifier 26 with respect to the same type of lubricants. The abscissa in FIG. 2 is a logarithmic axis indicating transmissivity (corresponding to the amount of the detection light). The ordinate indicates color sensor outputs (detection value). Both the transmissivity and the color sensor output in FIG. 2 are in arbitrary units. Supposing that a new lubricant results in a transmissivity value of one and a color sensor output value of one, FIG. 2 shows detection values in accordance with deterioration. The detection values sensed by the logarithmic amplifier 26 are indicated by a solid line connecting the plotted squares. The detection values sensed by the linear amplifier are indicated by a broken line connecting the plotted squares. The amount of the detection light received by the color sensor 22 may decrease as the transmissivity decreases in accordance with deterioration of the lubricant; therefore, the color sensor output from the logarithmic amplifier 26 may also decrease in accordance with the property of the color sensor 22 (the color sensor output may decrease almost constantly for the color sensor 22 used in this embodiment). As the transmissivity decreases in accordance with deterioration of the lubricant, the color sensor output from the linear amplifier may decrease sharply from the transmissivity of one and become almost constant from the transmissivity of about ⅒. Thus, even in a region of low lubricant transmissivity where the color sensor 22 may receive a small amount of light, the lubricant deterioration sensor 10 including the logarithmic amplifier 26 may allow sufficient amount of change of the color sensor output relative to the amount of change of the transmissivity of the lubricant. Therefore, even in a region where the color sensor 22 may receive a small amount of light, the difference in transmissivity of the lubricant or the amount of light can be clearly grasped from the color sensor output values.

Figure 3:
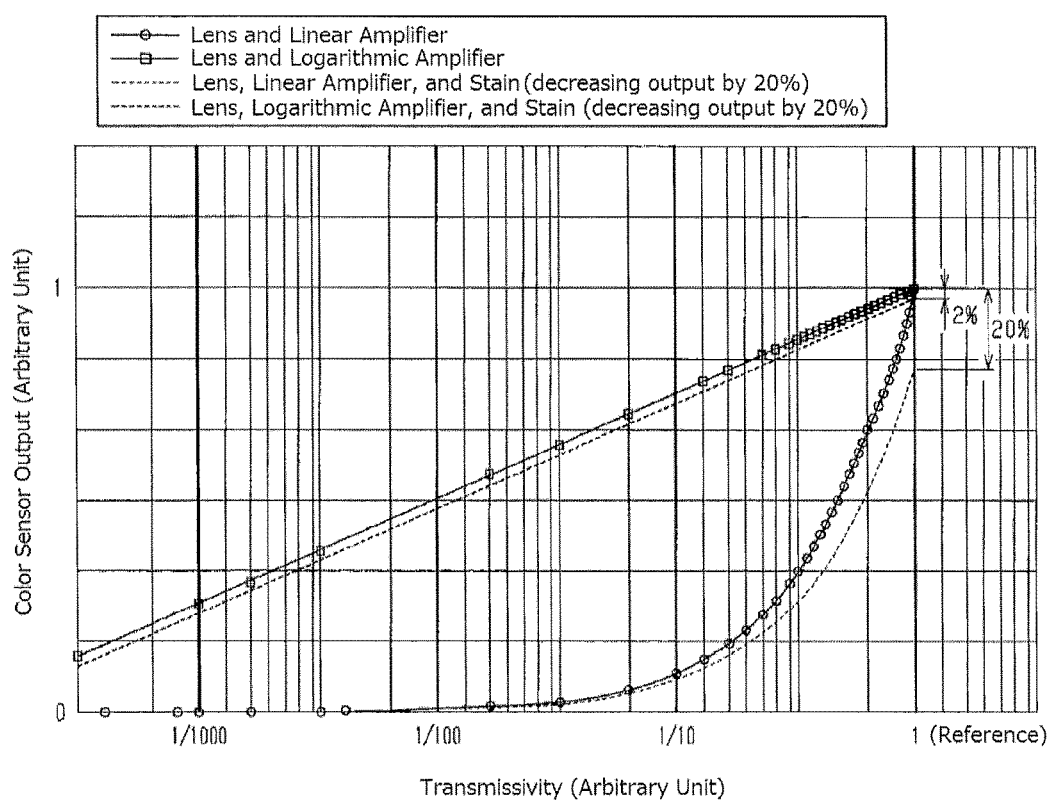
FIG. 3 shows the relationship between transmissivity and the output of a color sensor in the same embodiment of the lubricant deterioration sensor.

The structure of the optical sensor 20 may be as described above. FIG. 3 shows a diagram where the output results for a stained lubricant with the linear amplifier and the logarithmic amplifier are added into FIG. 2. For the stained lubricant, the color sensor output from the linear amplifier was decreased by 20% at the beginning of the detection as compared to the above new lubricant. The detection values for the new lubricant sensed by the linear amplifier are indicated by a solid line connecting the plotted circles. The detection values for the stained lubricant sensed by the linear amplifier are indicated by a thin broken line. The detection values for the stained lubricant sensed by the logarithmic amplifier are indicated by a thick broken line.

The color sensor output from the linear amplifier for the stained lubricant at the transmissivity of one is 20% less than the color sensor output from the linear amplifier for the new lubricant at the transmissivity of one. In contrast, the color sensor output from the logarithmic amplifier 26 for the same stained lubricant at the transmissivity of one is 2% less than the color sensor output from the logarithmic amplifier 26 for the new lubricant at the transmissivity of one. Therefore, even if the exit surface 23c or the incident surface 24a are stained, the amount of change of the color sensor output from the logarithmic amplifier 26 is large and thus the effect of stain can be restricted as compared to the linear amplifier.

Additionally, if the lubricant includes air bubbles, the detection values may be varied around the proper detection value due to presence of the detection light having passed through the air bubbles and the detection light not having passed through the air bubbles. However, since the lubricant deterioration sensor 10 including the logarithmic amplifier 26 allows a large amount of change of the color sensor output from the logarithmic amplifier 26, the effect of the air bubbles can be restricted as compared to the linear amplifier.

Further, when the oil entering gap 25 provided between the first prism 23 and the second prism 24 is widened, the light path is elongated and thus the detection values of the color sensor output may be decreased. However, since the lubricant deterioration sensor 10 including the logarithmic amplifier 26 allows a large amount of change of the color sensor output from the logarithmic amplifier 26, the detection can be performed with the oil entering gap 25 widened. Thus, even a lubricant having a high viscosity or a low fluidity can flow smoothly in the oil entering gap 25 provided between the first prism 23 and the second prism 24.

Figure 4:
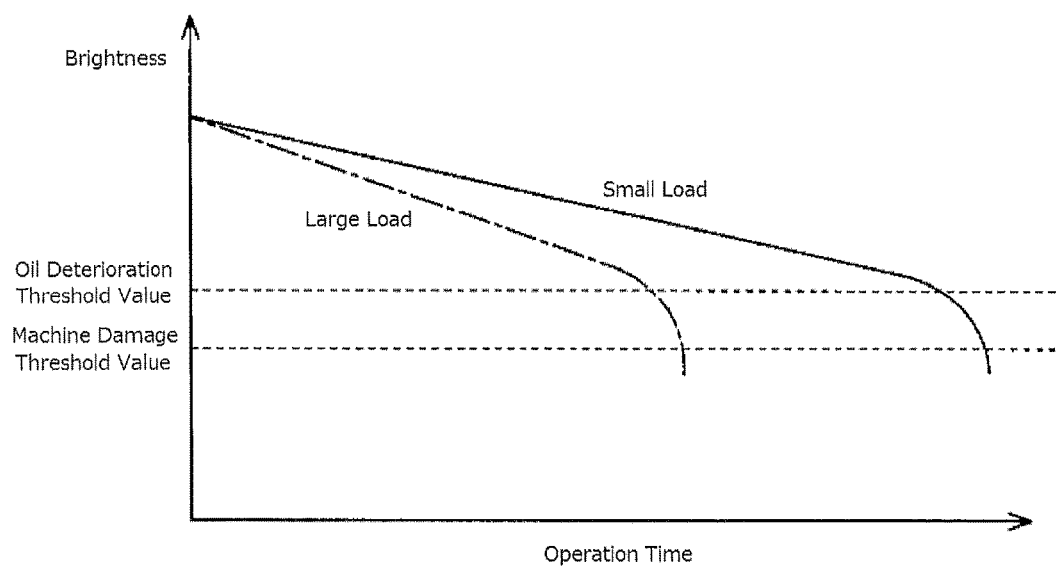
FIG. 4 shows the relationship between an operating time and brightness used for determining the deterioration of a lubricant in the same embodiment.

As illustrated in FIG. 4, the brightness may decrease as the operating time of the machine using the lubricant increases. The brightness ($\Delta E$) may be calculated from the formula (1) shown below of an R value, a G value, and a B value. The dashed-dotted line in FIG. 3 shows a change in the brightness with respect to the operating time when a load on a movable component of the machine is large. The solid line in FIG. 3 shows a change in the brightness with respect to the operating time when the load on the movable component of the machine is small. Since the brightness rapidly decreases with the deterioration, the deterioration of the lubricant can be grasped from the amount of change of the brightness per unit time.

Formula 1

The determination unit 31b may determine a deterioration state of the lubricant based on the brightness of the lubricant calculated from the detection value of the lubricant deterioration sensor 10. The brightness may correspond to the calculated value. More specifically, the determination unit 31 may determine the deterioration state of the lubricant based on comparison of the amount of change of the brightness per unit time to a predetermined value. If the deterioration of the lubricant is advanced, the determination unit 31 may determine the state of the lubricant based on the comparison between the brightness of the lubricant calculated from the detection value of the lubricant deterioration sensor 10 and an oil deterioration threshold value. The oil deterioration threshold value is used for determining whether the lubricant is deteriorated or not. When the brightness is less than or equal to the oil deterioration threshold value, the determination unit 31 may determine that the lubricant is deteriorated.

The determination unit 31 may determine the state of the machine based on the brightness of the lubricant calculated from the detection value of the lubricant deterioration sensor 10. More specifically, the determination unit 31 may determine the state of the machine based on comparison between the brightness of the lubricant calculated from the detection value of the lubricant deterioration sensor 10 and the machine damage threshold value. The machine damage threshold value may be used for determining whether the machine is damaged or not, and may be smaller than the oil deterioration threshold value. When the brightness is less than or equal to the machine damage threshold value, the determination unit 31 may determine that the lubricant is deteriorated.

Next, the method of determining the deterioration using the lubricant deterioration sensor 10 configured as above will now be described with reference to FIG. 5. The determination unit 31 may determine the deterioration state for each predetermined amount of the operation time of the machine having the lubricant deterioration sensor 10 installed therein. Alternatively, the state determination may be performed whenever need arises or only upon an instruction from a user.

Figure 5:
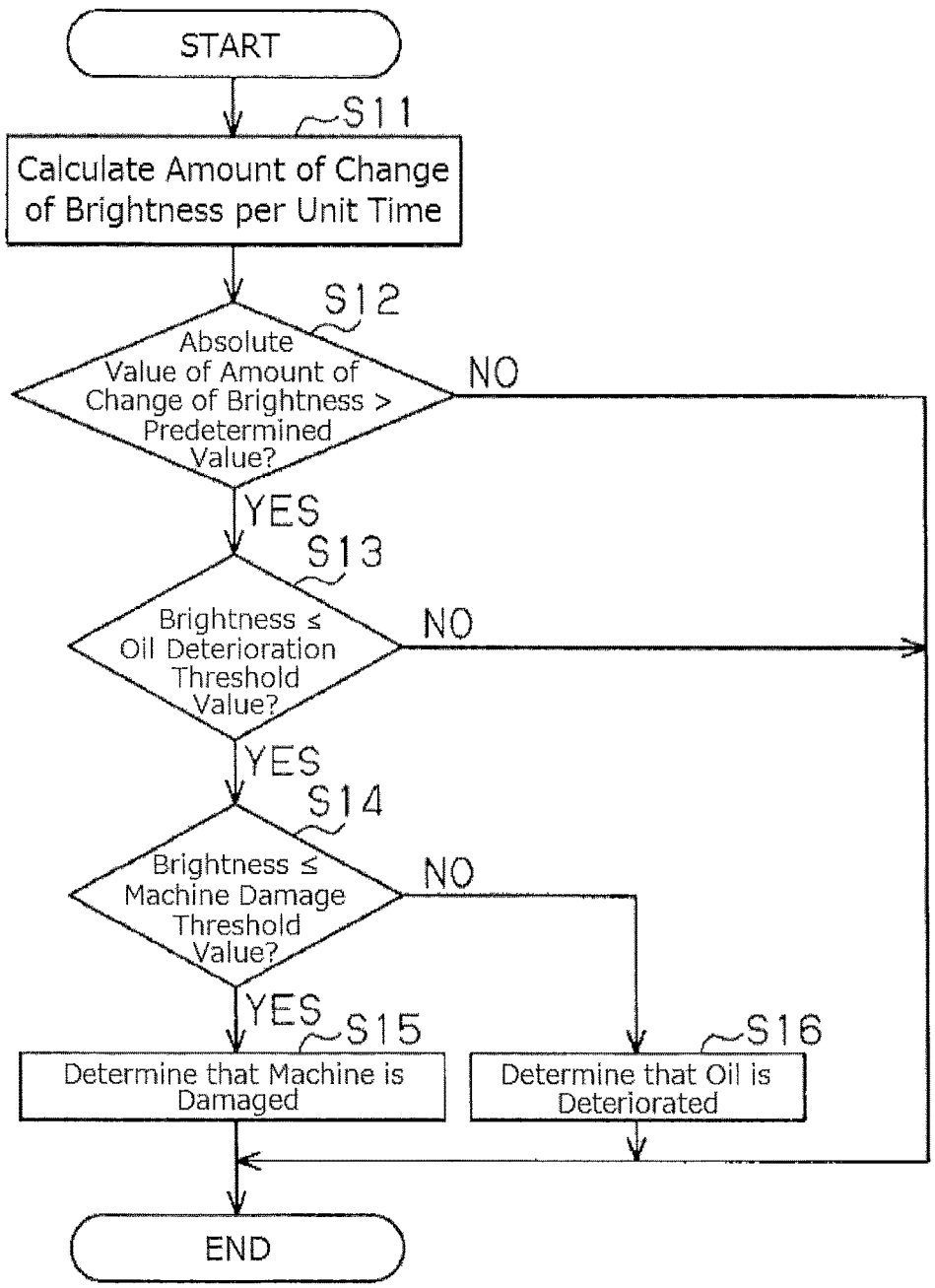
FIG. 5 is a flow chart showing a process of determining the deterioration of a lubricant in the same embodiment.

Referring to FIG. 5, the determination unit 31 may initiate a deterioration state determination in response to an instruction to perform the deterioration state determination. The determination unit 31 may calculate the brightness from the detection value of the lubricant deterioration sensor 10 and calculate the amount of change of the brightness per unit time (step S11). More specifically, the determination unit 31 may calculate current brightness from the detection value sensed by the color sensor 22 of the lubricant deterioration sensor 10 and calculate the amount of change from the brightness obtained unit time before and the current brightness. The amount of change may be calculated from the difference between the current brightness and the brightness obtained the unit time before.

The determination unit 31 may determine whether the absolute value of the amount of change of the brightness per unit time is larger than a predetermined value (step S12). More specifically, the determination unit 31 may perform comparison with the predetermined value that is larger than the absolute value of the amount of change during a short operation time, so as to determine whether the brightness has changed rapidly. Additionally, when the lubricant has deteriorated, the brightness may rapidly decrease relative to the operation time. If the absolute value of the amount of change of the brightness per unit time is smaller than the predetermined value (step S12: NO), the determination unit 31 may determine that there is no rapid change of the brightness and terminate the determination process.

In contrast, if the absolute value of the amount of change of the brightness per unit time is larger than the predetermined value (step S12: YES), the determination unit 31 may determine whether or not the brightness is less than or equal to the oil deterioration determination threshold value (step S13). More specifically, when the determination unit 31 determines that the brightness is larger than the oil deterioration determination threshold value (step S13: NO), the determination unit 31 may determine that the lubricant is not deteriorated and terminate the determination process.

When the determination unit 31 determines that the brightness is less than or equal to the oil deterioration determination threshold value (step S13: YES), the determination unit 31 determines whether or not the brightness is less than or equal to the machine damage threshold value (step S14). More specifically, when the determination unit 31 determines that the brightness is larger than the machine damage threshold value (step S14: NO), the determination unit 31 may determine that the lubricant is deteriorated (step S16) and terminate the determination process. In other words, when the brightness is larger than the machine damage threshold value and is less than or equal to the oil deterioration determination threshold value, the determination unit 31 determines that the lubricant is deteriorated but the machine is not damaged.

When the determination unit 31 determines that the brightness is less than or equal to the machine damage threshold value (step S14: YES), the determination unit 31 may determine that the machine is damaged (step S15) and terminate the determination process. In other words, when the brightness is less than or equal to the machine damage threshold value, the determination unit 31 may determine that the lubricant is contaminated with impurity substances due to damage to the machine and determine that the machine is damaged.

In the embodiment as described above, the brightness may be calculated from the detection value sensed by the lubricant deterioration sensor 10, and it is possible to easily determine the deterioration of the lubricant using the oil deterioration threshold value in addition to the amount of change of the brightness per unit time, and determine the damage to the machine using the machine damage threshold value.

According to the above-described embodiment, the following advantageous effects can be obtained. (1) The detection light emitted from the LED 21 may pass through the lubricant in the oil entering gap 25, and the color sensor 22 may sense the color information of the detection light having passed through the lubricant. The detection value sensed by the color sensor 22 may be amplified by the logarithmic amplifier 26 with a logarithmic function and outputted. The detection value amplified by the logarithmic amplifier 26 may change largely relative to the amount of change of the transmissivity in the region of low transmissivity as compared to the detection value amplified by the linear amplifier. Therefore, the transmissivity can be accurately determined from the detection value. Accordingly, it may be possible to maintain accuracy of sensing the deterioration state of a lubricant having low transmissivity.

(2) The collimator lens 29 for producing parallel light rays may be disposed between the LED 21 and the oil entering gap 25. The detection light emitted from the LED 21 may be transformed by the collimator lens 29 into parallel light rays, which can reach the color sensor 22 with restricted diffusion and convergence. Thus, the amount of light received by the color sensor 22 may be large enough to stabilize the sensing accuracy.

(3) It may be determined that the lubricant has been deteriorated if the absolute value of the amount of change of the brightness per unit time is larger than a predetermined value. Therefore, the determination can be accurately made from the amount of change of the brightness per unit time. It may be possible to grasp rapid deterioration of a lubricant and abnormality in a machine.

(4) It may be determined that the lubricant has been deteriorated if the absolute value of the amount of change of the brightness is larger than a predetermined value and the brightness is smaller than the oil deterioration threshold value. Therefore, the deterioration of the lubricant can be determined accurately from the amount of change of the brightness and the brightness itself.

(5) It may be determined that the lubricant has been deteriorated if the absolute value of the amount of change of the brightness is larger than a predetermined value and the brightness is smaller than a machine damage threshold value. Therefore, the damage to the machine can be determined accurately from the amount of change of the brightness and the brightness itself.

(Second Embodiment)

A second embodiment of a lubricant deterioration sensor will be hereinafter described with reference to FIGS. 6 and 7. The deterioration determination method using the lubricant deterioration sensor 10 according to this embodiment is different from the first embodiment in that a maximum color difference is used as the calculation value instead of the brightness. The following description will be focused on the difference from the first embodiment. The lubricant deterioration sensor 10 of this embodiment may have the same structure as the lubricant deterioration sensor 10 of the first embodiment shown in FIG. 1.

Figure 6:
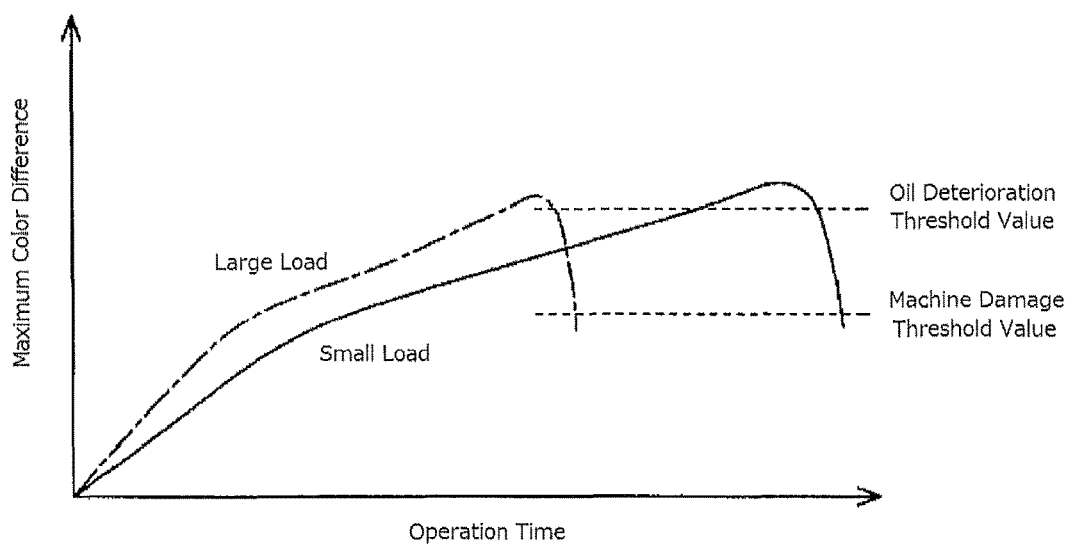
FIG. 6 shows the relationship between an operating time and a maximum color difference used for determining the deterioration of a lubricant in a second embodiment.

As illustrated in FIG. 6, the maximum color difference may increase with the operating time of the machine using the lubricant and then decrease once the maximum color difference reaches the extreme value. The dashed-dotted line in the figure shows a change in the maximum color difference with respect to the operating time when a load on a movable component of the machine is large. The solid line in the figure shows a change in the maximum color difference with respect to the operating time when the load on the movable component of the machine is small A maximum color-component difference (the maximum color difference) used for the state determination will be now described. The color component difference is an absolute value represented by |R−G|, |G−B|, or |R−B|. The maximum color difference is the largest among these color component differences. In other words, the maximum color difference is a difference between the maximum color component value and the minimum color component value. The minimum color component value generally corresponds to the B value and the maximum color component value generally corresponds to the R value among the R, G, B values, so only the color difference |R−B| may be calculated as the maximum color difference.

The determination unit 31 may determine the deterioration state of the lubricant based on the maximum color difference of the lubricant calculated from the detection value of the lubricant deterioration sensor 10. The maximum color difference may correspond to the calculated value. More specifically, the determination unit 31 may determine the deterioration state of the lubricant based on comparison of the amount of change of the maximum color difference per unit time to a predetermined value. When the predetermined value is zero and the amount of change is negative, it is determined that the deterioration of the lubricant is advanced. If the deterioration of the lubricant is advanced, the determination unit 31 may determine the deterioration state of the lubricant based on the maximum color difference of the lubricant calculated from the detection value of the lubricant deterioration sensor 10. More specifically, the determination unit 31 may determine the state of the lubricant based on comparison between the maximum color difference of the lubricant calculated from the detection value of the lubricant deterioration sensor 10 and the oil deterioration threshold value. The oil deterioration threshold value is used for determining whether the lubricant is deteriorated or not. When the maximum color difference is less than or equal to the oil deterioration determination threshold value, the determination unit 31 may determine that the lubricant is deteriorated.

The determination unit 31 may determine the state of the machine based on the maximum color difference of the lubricant calculated from the detection value of the lubricant deterioration sensor 10. More specifically, the determination unit 31 may determine the state of the machine based on comparison between the maximum color difference of the lubricant calculated from the detection value of the lubricant deterioration sensor 10 and the machine damage threshold value. The machine damage threshold value may be used for determining whether the machine is damaged or not, and may be smaller than the oil deterioration threshold value. When the maximum color difference is less than or equal to the machine damage threshold value, the determination unit 31 may determine that the machine is damaged.

Next, the method of determining the deterioration using the lubricant deterioration sensor 10 configured as above will now be described with reference to FIG. 7. The determination unit 31 may determine the deterioration state for each predetermined amount of the operation time of the machine having the lubricant deterioration sensor 10 installed therein. Alternatively, the state determination may be performed whenever need arises or only upon an instruction from a user.

Figure 7:
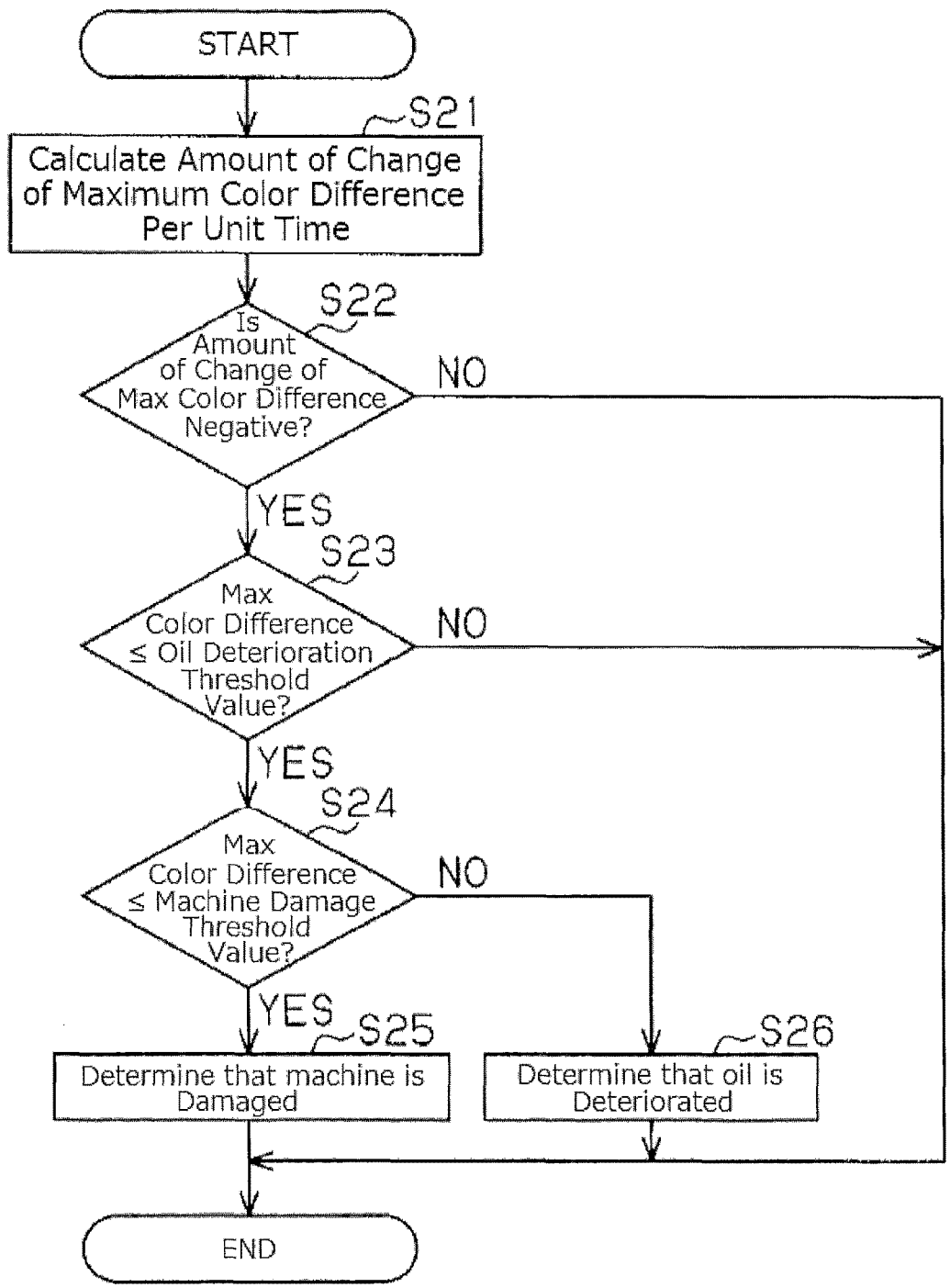
FIG. 7 is a flow chart showing a process of determining the deterioration of a lubricant in the same embodiment.

Referring to FIG. 7, the determination unit 31 may initiate a deterioration state determination in response to an instruction to perform the deterioration state determination. The determination unit 31 may calculate the brightness from the detection value of the lubricant deterioration sensor 10 and calculate the amount of change of the maximum color difference per unit time (step S21). More specifically, the determination unit 31 may calculate the current maximum color difference from the detection value sensed by the color sensor 22 of the lubricant deterioration sensor 10 and calculate the amount of change from the maximum color difference obtained the unit time before and the current maximum color difference. The amount of change may be calculated from the difference between the current maximum color difference and the maximum color difference obtained the unit time before.

The determination unit 31 may determine whether the amount of change of the maximum color difference per unit time is negative (step S22). When the lubricant is deteriorated, the maximum color difference increasing with the operation time may start decreasing once the maximum color difference reaches the extreme value. That is, the amount of change of the maximum color difference may turn from positive to negative. If the amount of change of the maximum color difference per unit time is positive (step S22: NO), the determination unit 31 may determine that there is no rapid change of the maximum color difference and terminate the determination process.

In contrast, if the amount of change of the maximum color difference per unit time is negative (step S22: YES), the determination unit 31 may determine whether or not the maximum color difference is less than or equal to the oil deterioration threshold value (step S23). More specifically, when the determination unit 31 determines that the maximum color difference is larger than the oil deterioration threshold value (step S23: NO), the determination unit 31 may determine that the lubricant is not deteriorated and terminate the determination process.

When the determination unit 31 determines that the maximum color difference is less than or equal to the oil deterioration threshold value (step S23: YES), the determination unit 31 determines whether or not the maximum color difference is less than or equal to the machine damage threshold value (step S24). More specifically, when the determination unit 31 determines that the maximum color difference is larger than the machine damage threshold value (step S24: NO), the determination unit 31 may determine that the lubricant is deteriorated (step S26) and terminate the determination process. In other words, when the maximum color difference is larger than the machine damage threshold value and is less than or equal to the oil deterioration threshold value, the determination unit 31 may determine that the lubricant is deteriorated but the machine is not damaged.

When the determination unit 31 determines that the maximum color difference is less than or equal to the machine damage threshold value (step S24: YES), the determination unit 31 may determine that the machine is damaged (step S25) and terminate the determination process. In other words, when the maximum color difference is less than or equal to the machine damage threshold value, the determination unit 31 may determine that the lubricant is contaminated with impurity substances due to damage to the machine and determine that the machine is damaged.

In the embodiment as described above, the maximum color difference may be calculated from the detection value sensed by the lubricant deterioration sensor 10, and it is possible to easily determine the deterioration of the lubricant using the oil deterioration threshold value in addition to the amount of change of the maximum color difference per unit time, and determine the damage to the machine using the machine damage threshold value.

According to the above-described embodiment, the following advantageous effects can be obtained in addition to the advantages (1) and (2) of the first embodiment. (3) It may be determined that the lubricant has been deteriorated if the amount of change of the maximum color difference per unit time is a negative value. Therefore, the determination can be accurately made from the amount of change of the maximum color difference per unit time.

(4) It may be determined that the lubricant has been deteriorated if the amount of change of the maximum color difference is negative and the maximum color difference is smaller than the oil deterioration threshold value. Therefore, the deterioration of the lubricant can be determined accurately from the amount of change of the maximum color difference and the maximum color difference itself.

(5) It may be determined that the lubricant has been deteriorated if the amount of change of the maximum color difference is negative and the maximum color difference is smaller than a machine damage threshold value. Therefore, the damage to the machine can be determined accurately from the amount of change of the maximum color difference and the maximum color difference itself.

(Third Embodiment)

A third embodiment of a lubricant deterioration sensor will be hereinafter described with reference to FIGS. 8 and 9. The deterioration determination method using the lubricant deterioration sensor 10 according to this embodiment is different from the first embodiment in that the maximum color difference and the brightness are used as the calculation value. The following description will be focused on the difference from the first embodiment. The lubricant deterioration sensor 10 of this embodiment may have the same structure as the lubricant deterioration sensor 10 of the first embodiment shown in FIG. 1.

Figure 8:
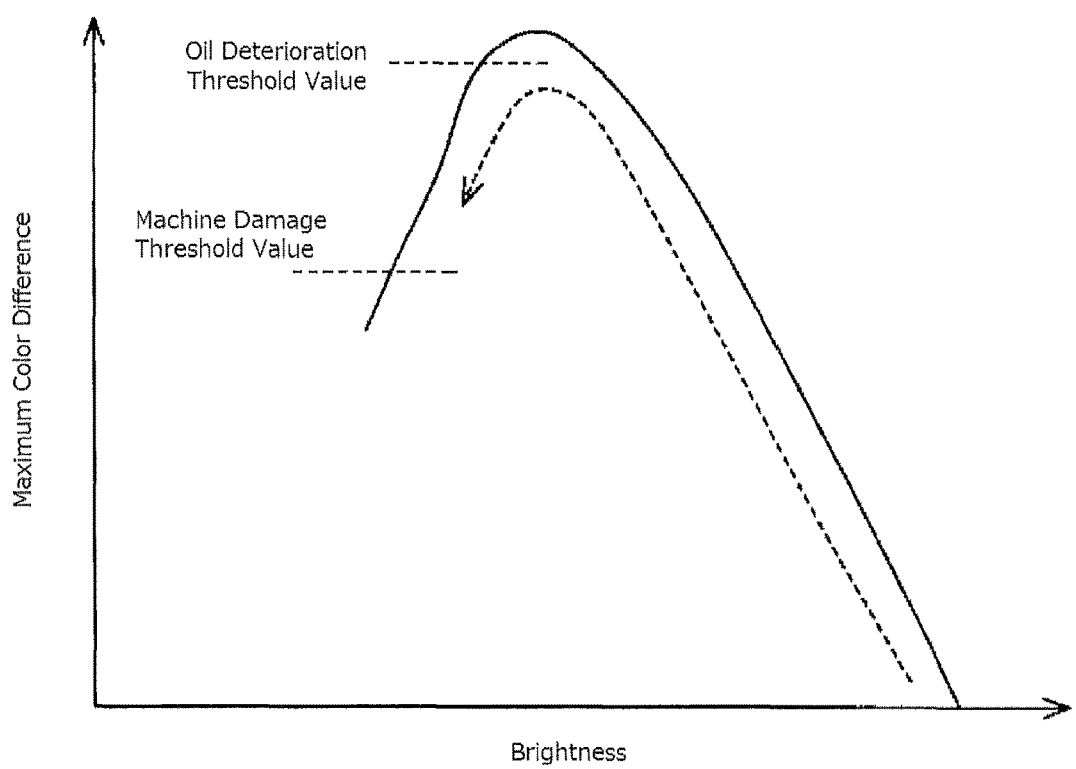
FIG. 8 shows the relationship between brightness and a maximum color difference used for determining the deterioration of a lubricant in a third embodiment.

In FIG. 8, the abscissa indicates the brightness and the ordinate indicates the maximum color difference. The brightness may decrease with the operation time of the machine using the lubricant. The maximum color difference may increase as the brightness of the lubricant decreases, and may decrease once the maximum color difference reaches the extreme value.

The determination unit 31 may determine the deterioration state of the lubricant based on the brightness and the maximum color difference of the lubricant calculated from the detection value of the lubricant deterioration sensor 10. The brightness and the maximum color difference may correspond to the calculated value. More specifically, the determination unit 31 may determine the deterioration state of the lubricant based on comparison of the amount of change of the maximum color difference per unit brightness to a predetermined value. When the predetermined value is zero and the amount of change is negative, it is determined that the deterioration of the lubricant is advanced. If the deterioration of the lubricant is advanced, the determination unit 31 may determine the deterioration state of the lubricant based on the maximum color difference relative to the brightness of the lubricant calculated from the detection value of the lubricant deterioration sensor 10. More specifically, if the deterioration of the lubricant is advanced, the determination unit 31 may determine the state of the lubricant based on the comparison between the maximum color difference of the lubricant calculated from the detection value of the lubricant deterioration sensor 10 and an oil deterioration threshold value. The oil deterioration threshold value is used for determining whether the lubricant is deteriorated or not. When the maximum color difference is less than or equal to the oil deterioration threshold value, the determination unit 31 may determine that the lubricant is deteriorated.

The determination unit 31 may determine the state of the machine based on the maximum color difference relative to the brightness of the lubricant calculated from the detection value of the lubricant deterioration sensor 10. More specifically, the determination unit 31 may determine the state of the machine based on comparison between the maximum color difference of the lubricant calculated from the detection value of the lubricant deterioration sensor 10 and the machine damage threshold value. The machine damage threshold value is used for determining whether the machine is damaged or not and is smaller than the oil deterioration threshold value. When the maximum color difference is less than or equal to the machine damage threshold value, the determination unit 31 may determine that the machine is damaged.

Next, the method of determining the deterioration using the lubricant deterioration sensor 10 configured as above will now be described with reference to FIG. 9. The determination unit 31 may determine the deterioration state for each predetermined amount of the operation time of the machine having the lubricant deterioration sensor 10 installed therein. Alternatively, the state determination may be performed whenever need arises or only upon an instruction from a user.

Figure 9:
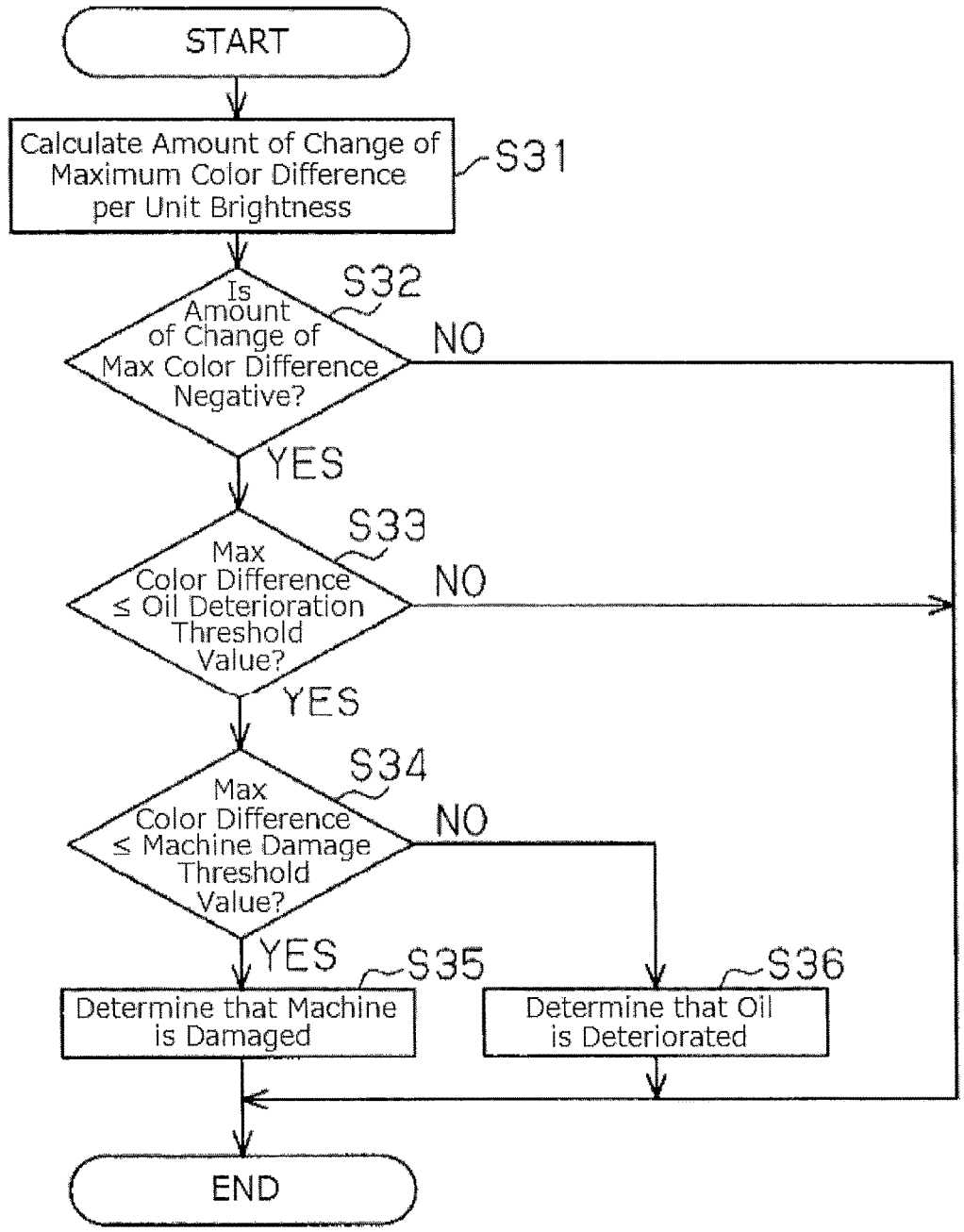
FIG. 9 is a flow chart showing a process of determining the deterioration of a lubricant in the same embodiment.
Figure 10:
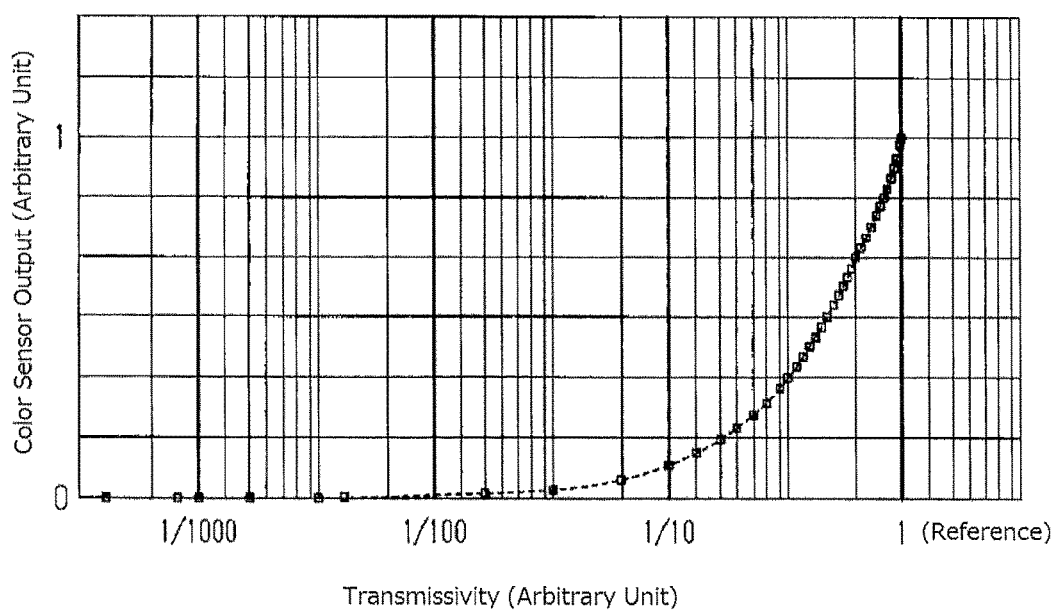
FIG. 10 shows the relationship between transmissivity and the output of a color sensor in a conventional lubricant deterioration sensor.

Referring to FIG. 9, the determination unit 31 may initiate a deterioration state determination in response to an instruction to perform the deterioration state determination. The determination unit 31 may calculate the brightness and the maximum color difference from the detection value of the lubricant deterioration sensor 10 and calculate the amount of change of the maximum color difference per unit brightness (step S31). More specifically, the determination unit 31 may calculate the current brightness and the current maximum color difference from the detection value sensed by the color sensor 22 of the lubricant deterioration sensor 10 and calculate the amount of change from the maximum color difference obtained the unit brightness before and the current maximum color difference. The amount of change may be calculated from the difference between the current maximum color difference and the maximum color difference obtained the unit brightness before.

The determination unit 31 may determine whether the amount of change of the maximum color difference per unit brightness is negative (step S32). When the lubricant is deteriorated, the maximum color difference increasing as the brightness decreases may start decreasing once the maximum color difference reaches the extreme value. That is, the amount of change of the maximum color difference may turn from positive to negative. If the amount of change of the maximum color difference per unit brightness is positive (step S32: NO), the determination unit 31 may determine that there is no rapid change of the maximum color difference and terminate the determination process.

In contrast, if the amount of change of the maximum color difference per unit brightness is negative (step S32: YES), the determination unit 31 may determine whether or not the maximum color difference is less than or equal to the oil deterioration threshold value (step S33). More specifically, when the determination unit 31 determines that the maximum color difference is larger than the oil deterioration threshold value (step S33: NO), the determination unit 31 may determine that the lubricant is not deteriorated and terminate the determination process.

When the determination unit 31 determines that the maximum color difference is less than or equal to the oil deterioration threshold value (step S33: YES), the determination unit 31 determines whether or not the maximum color difference is less than or equal to the machine damage threshold value (step S34). More specifically, when the determination unit 31 determines that the maximum color difference is larger than the machine damage threshold value (step S34: NO), the determination unit 31 may determine that the lubricant is deteriorated (step S26) and terminate the determination process. In other words, when the maximum color difference is larger than the machine damage threshold value and is less than or equal to the oil deterioration threshold value, the determination unit 31 may determine that the lubricant is deteriorated but the machine is not damaged.

When the determination unit 31 determines that the maximum color difference is less than or equal to the machine damage threshold value (step S34: YES), the determination unit 31 may determine that the machine is damaged (step S35) and terminate the determination process. In other words, when the maximum color difference is less than or equal to the machine damage threshold value, the determination unit 31 may determine that the lubricant is contaminated with impurity substances due to damage to the machine and determine that the machine is damaged In the embodiment as described above, the brightness and the maximum color difference may be calculated from the detection value sensed by the lubricant deterioration sensor 10, and it is possible to easily determine the deterioration of the lubricant using the oil deterioration threshold value in addition to the amount of change of the maximum color difference per unit brightness, and determine the damage to the machine using the machine damage threshold value.

According to the above-described embodiment, the following advantageous effects can be obtained in addition to the advantages (1) and (2) of the first embodiment. (3) It may be determined that the lubricant has been deteriorated if the amount of change of the maximum color difference per unit brightness is a negative value. Therefore, the determination can be accurately made from the amount of change of the maximum color difference per unit brightness.

(4) It may be determined that the lubricant has been deteriorated if the amount of change of the maximum color difference per unit brightness is negative and the maximum color difference per unit brightness is smaller than the oil deterioration threshold value. Therefore, the deterioration of the lubricant can be determined accurately from the amount of change of the maximum color difference per unit brightness and the maximum color difference itself per unit brightness.

(5) It may be determined that the lubricant has been deteriorated if the amount of change of the maximum color difference per unit brightness is negative and the maximum color difference per unit brightness is smaller than the machine damage threshold value. Therefore, the damage to the machine can be determined accurately from the amount of change of the maximum color difference per unit brightness and the maximum color difference itself per unit brightness.

The above-described embodiments can be appropriately modified as described below. In the first embodiment, the amount of change of the brightness per unit time is calculated, and it is determined that the lubricant is deteriorated if the absolute value of the amount of change of the brightness is larger than a predetermined value. However, if the deterioration of the lubricant can be sufficiently determined only from the calculated brightness, it is not necessary to make the determination based on the amount of change of the brightness per unit time.

In the second embodiment, the amount of change of the maximum color difference per unit time is calculated, and it is determined that the lubricant is deteriorated if the amount of change of the maximum color difference is negative. However, if the deterioration of the lubricant can be sufficiently determined only from the calculated maximum color difference, it is not necessary to make the determination based on the amount of change of the maximum color difference per unit time.

In the third embodiment, the amount of change of the maximum color difference per unit brightness is calculated, and it is determined that the lubricant is deteriorated if the amount of change of the maximum color difference is negative. However, if the deterioration of the lubricant can be sufficiently determined only from the calculated maximum color difference, it is not necessary to make the determination based on the amount of change of the maximum color difference per unit brightness.

In the above embodiments, the damage to the machine is determined from the deterioration of the lubricant, but if the determination of the damage to the machine is not necessary, it may be possible to determine only the deterioration of the lubricant. In the above embodiments, the deterioration level of the lubricant is determined based on the brightness or the maximum color-component difference. However, it may be possible to determine the deterioration level of the lubricant based on calculation values other than the brightness and the maximum color-component difference.

In the above embodiments, an external device such as PC30 located outside the optical sensor 20 may be used as the determination unit 31, but it may be possible to dispose the determination unit 31 in the optical sensor 20. In the above embodiments, a collimator lens 29 may be disposed between the LED 21 and the first prism 23 of the first through hole 11c. However, if a sufficient amount of detection light reaches the color sensor 22, the collimator lens 29 can be omitted.

In the above embodiments, the optical sensor may have the reflection type structure using a prism. However, other optical sensors such as those having the light emitting element and the light receiving element faced with each other may also be used. The above embodiments may be applied to machines having a bearing or piston operating with a lubricant, or machines such as wind generators, construction machines, aircraft, railroad vehicles, or vacuum pumps. More specifically, the wind generator may include, for example, a step-up gear and its bearing for the wind generator, a pitch-driving hydraulic cylinder and a reduction gear, and a YAW driving hydraulic motor. As for the construction machine, it may include, for example, a hydraulic motor, a hydraulic cylinder, a hydraulic valve (a load sensing valve and the like), a drive motor, a rotary motor, a joint and the like. As for the aircraft, it may include, for example, a flight control actuator, a hydraulic motor and the like that drives a spoiler, an aileron, an elevator, an ladder, a flap, a slat, a brake, a steering and the like. As for the railroad vehicle, it may include, for example, an air compressor for the railroad vehicles. As for a commercial vehicle and a passenger vehicle, they may include, for example, a brake actuator, a circulation pump for an engine oil, a supply pump for fuel and the like. As for a vessel, it may include, for example, a circulation pump for an engine oil, a supply pump for fuel, a hydraulically-actuated device and equipment, and the like.

In the above embodiments, the object of inspection is a lubricant, but may also be cooling oil or the like.

LIST OF REFERENCE NUMBERS 10 lubricant deterioration sensor
11 housing
11a container section
11b bottom surface
11c first through hole
11d second through hole
16 circuit substrate
17 cover
20 optical sensor
21 LED as a light emitting element
22 color sensor as a light receiving element
23 first prism
23a incident surface
23b reflection surface
23c exit surface
24 second prism
24a incident surface
24b reflection surface
24c exit surface
25 oil entering gap as an inspection unit
26 logarithmic amplifier
28 LED driver
29 collimator lens
30 PC
31 determination unit

What is claimed is:

1. A lubricant deterioration sensor used for sensing a deterioration state of a lubricant, comprising:
an inspection unit for receiving a lubricant to be inspected;
a light emitting element for emitting detection light into the inspection unit and through the lubricant;
a light receiving element for obtaining a detection value indicating color information of the detection light having passed through the lubricant, wherein the detection light that has passed through the lubricant includes a wavelength region corresponding to the physical color absorbed by the lubricant; and
a logarithmic amplifier for amplifying the detection value with a logarithmic function and outputting the amplified detection value.

2. The lubricant deterioration sensor according to claim 1, further comprising a collimator lens disposed between the light emitting element and the inspection unit and configured to emit parallel light rays.

3. The lubricant deterioration sensor according to claim 1, further comprising a determination unit configured to calculate brightness from the detection value and determine that the lubricant is deteriorated if an absolute value of an amount of change of the brightness per unit time is larger than a predetermined value.

4. The lubricant deterioration sensor according to claim 1, further comprising a determination unit configured to calculate a maximum color-component difference from the detection value and determine that the lubricant is deteriorated if an amount of change of the maximum color-component difference per unit time is a negative value.

5. The lubricant deterioration sensor according to claim 1, further comprising a determination unit configured to calculate brightness and a maximum color-component difference from the detection value and determine that the lubricant is deteriorated if an amount of change of the maximum color-component difference per unit brightness is a negative value.

6. The lubricant deterioration sensor according to claim 3, wherein the determination unit determines that the lubricant is deteriorated if the absolute value of the amount of change of the brightness is larger than a predetermined value and the brightness is smaller than an oil deterioration threshold value for determining deterioration of the lubricant.

7. The lubricant deterioration sensor according to claim 3, wherein the determination unit determines that a machine is damaged if the absolute value of the amount of change of the brightness is larger than a predetermined value and the brightness is smaller than a machine damage threshold value for determining damage to the machine on which the lubricant deterioration sensor is installed.

8. The lubricant deterioration sensor according to claim 1, wherein the inspection unit is configured to retain the lubricant therein as the detection light passes through the lubricant.

9. The lubricant deterioration sensor according to claim 1, wherein the inspection unit includes a gap in which the lubricant is retained as the detection light passes through the lubricant.

10. The lubricant deterioration sensor according to claim 1, wherein the detection light is transformed into parallel light rays, and the inspection unit includes a gap in which the lubricant is retained as the parallel light rays pass through the lubricant.

* * * * *